United States Patent
Ivanova

(10) Patent No.: US 8,329,146 B2
(45) Date of Patent: Dec. 11, 2012

(54) HAIR TREATMENT COMPOSITION COMPRISING A PRESSURE SENSITIVE ADHESIVE

(75) Inventor: Katya Ivanova, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 489 days.

(21) Appl. No.: 12/086,452

(22) Filed: Jun. 12, 2008

(65) Prior Publication Data

US 2010/0284941 A1      Nov. 11, 2010

(30) Foreign Application Priority Data

Dec. 22, 2005   (EP) .................................... 05257987

(51) Int. Cl.
*A61K 8/00*   (2006.01)
*A61K 9/00*   (2006.01)
(52) U.S. Cl. ...................................................... 424/47
(58) Field of Classification Search ..................... 424/47
See application file for complete search history.

(56) References Cited

U.S. PATENT DOCUMENTS

| | | | | |
|---|---|---|---|---|
| 5,021,477 A | | 6/1991 | Garbe et al. .................... | 424/70 |
| 5,166,276 A | * | 11/1992 | Hayama et al. ............ | 525/329.7 |
| 2004/0057923 A9 | * | 3/2004 | Rollat et al. ............... | 424/70.16 |

FOREIGN PATENT DOCUMENTS

| | | |
|---|---|---|
| EP | 0 408 311 | 1/1991 |
| EP | 0 412 704 | 2/1991 |
| EP | 0 412 707 | 2/1991 |
| WO | 02/03933 | 1/2002 |
| WO | 02/03935 | 1/2002 |
| WO | 03/28677 | 4/2003 |
| WO | 2004/084846 | 10/2004 |
| WO | WO 2004084846 A1 * | 10/2004 |

OTHER PUBLICATIONS

PCT International Search Report in PCT application PCT/EP2006/011386.
Co-pending Application: Applicant: Ivanova; U.S. Appl. No. 12/084,397; (EP 05256820).
Co-pending Application: Applicant: Ivanova; U.S. Appl. No. 12/084,398; (EP 05256819).
PCT International Search Report in PCT application PCT/EP2006/009062.
PCT International Search Report in PCT application PCT/EP2006/9066.
EP Search Report in EP application EP 05256820.

* cited by examiner

*Primary Examiner* — Johann Richter
*Assistant Examiner* — Thor Nielsen
(74) *Attorney, Agent, or Firm* — Ronald A. Koatz

(57) ABSTRACT

A hair treatment composition comprising an acrylic pressure sensitive adhesive.

5 Claims, No Drawings

HAIR TREATMENT COMPOSITION COMPRISING A PRESSURE SENSITIVE ADHESIVE

FIELD OF THE INVENTION

This invention relates to hair treatment compositions and to their use in the treatment of hair.

BACKGROUND AND PRIOR ART

Pressure sensitive adhesives (PSAs) have been used in hair care compositions as described in U.S. Pat. No. 5,166,276, EP408311, EP412707 and EP412704. However these PSAs tend to hydrolyse in aqueous and hydroalcoholic hair care products.

WO2004/084846 and co-pending applications EP05256819 and EP05256820 disclose hair styling compositions comprising silicone pressure sensitive adhesives, however there is still a need to provide formulations comprising sensitive pressure sensitive adhesives with improved feel.

Furthermore the silicone pressure sensitive adhesives of the prior art have a detrimental effect on the foaming properties of some mousse products. The present invention enables products to be formed with superior foaming, yet having the positive sensory effects of PSAs described in the citations above.

SUMMARY OF THE INVENTION

Accordingly, this invention provides a hair treatment composition comprising an acrylic pressure sensitive adhesive.

A method for styling hair is also described which comprises contacting the hair with the composition described above.

DETAILED DESCRIPTION OF THE INVENTION

Unless specified otherwise, all wt % values quoted hereinafter are percentages by weight based on total weight of the hair treatment composition.

Pressure Sensitive Adhesives

This present invention relates to hair treatment compositions comprising an acrylic pressure sensitive adhesive.

"Pressure sensitive adhesive" (PSA) materials are permanently tacky at room temperature and able to develop measurable adhesion to a surface simply upon contact or by the application of a light pressure. Generally they do not require heat. No chemical reaction takes place between the adhesive and the adherent, no curing of the adhesive is necessary and no solvent is required to be lost during the adhesion process.

Acrylic PSAs are random copolymers comprising an acrylic group having a side-chain with at least 4 carbons (eg n-butyl acrylate or 2-ethylhexyl acrylate) and having a low glass transition temperature Tg, a short side-chain acrylic such as methyl acrylate to adjust the Tg, and acrylic acid to improve adhesion and optimise elongational properties (i.e., their mechanical response to deformation in uniaxial extension). Small molecule additives such as tackifiers may be included, essentially to adjust the Tg and optimise dissipative properties but are not essential.

The acrylic sensitive pressure adhesive is preferably in the form of an emulsion.

Suitable water-born acrylic sensitive pressure adhesives include Dow Corning PA-0560, Dow Corning PA-0580, Dow Corning MG-0560, Dow Corning MG-0580, Tackwhite NA 55 ex Ichemco srl, Tackwhite A 4 MED ex Ichemco srl NACOR 38-088A ex National Starch & Chemical, Acronal 80 D ex BASF AG, Acronal 85 D BASF AG, Acronal A220 exBASF AG, Acronal N 285 ex BASF AG, Acronal V 210 ex BASF AG and Acronal V212 ex BASF AG.

Suitable solvent born acrylic sensitive pressure adhesives include
PA-0607 ex Dow Corning, PA-0610 ex Dow Corning,
MG-0607 ex Dow Corning, MG-0610 ex Dow Corning,
Duro Tak 387-2353/87-2353 ex National Starch
Duro-Tak 387-2510/87-2510 ex National Starch
Duro-Tak 87-900A ex National Starch
Duro-Tak 87-9301 ex National Starch
Duro-Tak 87-200A ex National Starch
Solacril 742 ex Ichemo srl
Solucryl 147 ex UCB Chemicals
Solucryl 380 ex UCB Chemicals
Gelva 737 ex Monsanto Preferably the acrylic pressure sensitive adhesive is present at levels from 0.01% to 10% by weight of the total composition. More preferred amounts of acrylic pressure sensitive adhesive in the compositions of the invention are from 0.1% to 5% by weight of the composition, even more preferably from 0.5% to 3% by weight.

Hair Styling Polymer

The compositions of the invention may optionally comprise from 0.001% to 10% by weight of a hair styling polymer. More preferred amounts of hair styling polymer in the compositions of the invention are from 0.1% to 5% by weight of the composition, even more preferably from 0.5% to 3% by weight.

Hair styling polymers are well known. Suitable hair styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Surfactant

The compositions of the invention may comprise surfactant in addition to that required for the preparation of any PSA emulsion. The surfactants which are suitable for use in the compositions of the invention may be nonionic, cationic, anionic, zwitterionic or a mixture of such surfactants depending on the product form.

The hair styling compositions of the invention preferably comprise a non-ionic surfactant, in an amount of up to 5%, preferably from 0.01% to 1%, most preferably from 0.02% to 0.8% by weight based on total weight.

Examples of suitable non-ionic surfactants are condensation products of aliphatic ($C_8$-$C_{18}$) primary or secondary linear or branched chain alcohols or phenols with alkylene oxides, usually ethylene oxide and generally having at least 15, preferably at least 20, most preferably from 30 to 50 ethylene oxide groups. Other suitable non-ionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates.

Of particular use are those non-ionic surfactants of general formula R(EO)$_x$H, where R represents a straight or branched chain alkyl group having an average carbon chain length of 12-18 carbon atoms and x ranges from 30 to 50. Specific examples include steareth-40, steareth-50, ceteareth-30, ceteareth-40, ceteareth-50 and mixtures thereof. Suitable commercially available examples of these materials include Unicol SA-40 (Universal Preserv-A-Chem), Empilan KM50

(Albright and Wilson), NONION PS-250 (Nippon Oils & Fats), Volpo CS50 (Croda Inc), and Incropol CS-50 (Croda Inc).

Water

Compositions of the present invention can also include water, preferably distilled or de-ionised, as a carrier for the PSAs. Water is preferably used as an emulsion when used as a carrier for acrylic PSAs. It may additionally be a carrier or a solvent for other components. When present the water will typically be present in amounts ranging from 30% to 98%, preferably from 50% to 95% by weight.

Solvent/Carrier

Compositions of the present invention can also include solvents, as a carrier or solvent for the acrylic PSAs and other components. When present the solvent will typically be present in amounts ranging from 30% to 98%, preferably from 50% to 95% by weight. Examples of solvents are hydrocarbons, esters, alcohols etc. Particularly preferred solvents include ethyl acetate and isopropanol.

Emollients

Emollients such as hydrocarbons, esters, silicone fluids, may be included in the compositions of the invention. Emollients may typically be present in compositions of the invention in amounts of from 0.001% to 10% by weight, preferably 0.1% to 3% by weight. Emollients may be single compounds or mixtures of two or more compounds from the same class or different general classes.

Emollients may be included in any of the compositions of the invention, regardless of whether they contain a hair styling polymer. In one embodiment of the invention, the compositions (such as aerosol mousse formulations, for example) comprise a hair conditioning agent and are substantially free of hair styling polymer.

Suitable hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Suitable oily or fatty materials are selected from hydrocarbon oils, fatty esters and mixtures thereof. Straight chain hydrocarbon oils will preferably contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as $C_1$-$C_{22}$ carboxylic acids. Preferred materials include cocoa butter, palm stearin, sunflower oil, soyabean oil and coconut oil.

Especially preferred is isopropyl myristate.

The oily/fatty material is suitably present at a level of from 0.05 to 10, preferably from 0.2 to 5, more preferably from about 0.5 to 3 wt %.

Examples of suitable silicone based emollients useful herein can include either cyclic or linear polydimethylsiloxanes, phenyl and alkyl phenyl silicones, and silicone copolyols. Cationic conditioning agents useful herein can include quaternary ammonium salts or the salts of fatty amines, such as cetyl ammonium chloride, for example.

Compositions according to the invention may, optionally, comprise from 0.1% to 10% by weight of a volatile silicone as the hair conditioning agent. Volatile silicones are well known in the art and are commercially available and include, for example linear and cyclic compounds. Volatile silicone oils are preferably linear or cyclic polydimethylsiloxanes containing from about three to about nine silicon atoms.

The compositions of the invention may optionally comprise a cross-linked silicone polymer.

The cross-linked silicone polymer is preferably a non-rigid emulsion-polymerised and may be present in compositions of the invention in an amount of up to 10% by weight based on the total weight of the composition, more preferably from 0.2% to 6% by weight, most preferably from 0.5 to 5% by weight.

Preferred silicone polymers for use in the invention are polydiorganosiloxanes, preferably derived from suitable combinations of $R_3SiO_{0.5}$ units and $R_2SiO$ units where each R independently represents an alkyl, alkenyl (e.g., vinyl), alkaryl, aralkyl, or aryl (e.g. phenyl) group. R is most preferably methyl.

The preferred silicone polymers of the invention are cross-linked polydimethyl siloxanes (which have the CTFA designation dimethicone), and cross-linked polydimethyl siloxanes having end groups such as hydroxyl (which have the CTFA designation dimethiconol). Good results have been obtained with cross-linked dimethiconol.

Cross-linking of the silicone polymer is typically introduced concurrently during emulsion polymerisation of the polymer through the inclusion of the required amount of trifunctional and tetrafunctional silane monomer units, for example, those of formula:

R Si (OH)$_3$ wherein R represents an alkyl, alkenyl (e.g. vinyl), alkaryl, aralkyl or aryl (e.g. phenyl) group, preferably methyl.

The degree of cross-linking of the silicone polymer can be measured as the percentage of branched monomer units in the silicone polymer and is from 0.05% to 10%, preferably being in the range 0.15% to 7%, e.g. from 0.2% to 2%. Increasing cross-linking is found to improve styling benefits but also to reduce conditioning performance somewhat, so compromise levels must be selected with properties optimised to suit consumer preferences in different cases. Good overall performance has been obtained with dimethiconol 0.3% cross-linked.

Suitable emulsion polymerised cross-linked silicone polymers are commercially available or can be readily made using conventional techniques well known to those skilled in the art.

Cross-linked silicone polymers are described in EP 818190, the contents of which are incorporated herein by reference.

Cationic Conditioning Agents

The compositions of the invention may optionally comprise cationic surfactants, used singly or in admixture.

Cationic surfactants useful in compositions of the invention contain amino or quaternary ammonium hydrophilic moieties, which are positively charged when, dissolved in the aqueous composition of the present invention.

Examples of suitable cationic surfactants are those corresponding to the formula:

$$[N(R_1)(R_2)(R_3)(R_4)]^+(X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the formula:

$$[N(R_5)(R_6)(R_6)(R_7)(R_8)]^+(X)^-$$

in which $R_5$ is a hydrocarbyl chain having 8 to 14 carbon atoms or a functionalized hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalized hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsuiphate radicals.

The functionalised hydrocarbyl chains (b) may suitably contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:

(i) lauryl trimethylammonium chloride (available commercially as Arquad C35 ex-Akzo); cocodimethyl benzyl ammonium chloride (available commercially as Arquad DMCB-80 ex-Akzo)

(ii) compounds of the formula:

$$[N(R_1)(R_2)((CH_2CH_2O)_xH)((CH_2CH_2O)_yH)]^+(X)^-$$

wherein:
x+y is an integer from 2 to 20;
$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;
$R_2$ is a $C_1$-$C_3$ alkyl group or benzyl group, preferably methyl, and
X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo)

(iii) compounds of the formula:

$$[N(R_1)(R_2)(R_3)((CH_2)_nOH)]^+(X)^-$$

wherein:
n is an integer from 1 to 4, preferably 2;
$R_1$ is a hydrocarbyl chain having 8 to 14, preferably 12 to 14, most preferably 12 carbon atoms;
$R_2$ and $R_3$ are independently selected from $C_1$-$C_3$ alkyl groups, and are preferably methyl, and
$X^-$ is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing cationic surfactants compounds may also be suitable.

Examples of suitable cationic surfactants include:
quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride
Quaternium –5
Quaternium –31
Quaternium –18
and mixtures thereof.

In the conditioners of the invention, the level of cationic surfactant is preferably from 0.01 to 10, more preferably 0.05 to 5, most preferably 0.1 to 2 wt % of the total composition.

Product Form

Compositions of the present invention are formulated into hair styling compositions which may take a variety of forms, including, for example, mousses, gels, lotions, creams, sprays and tonics. These product forms are well known in the art.

The preferred product is a spray and/or aerosol and/or mousse.

The compositions of the invention are preferably foaming compositions. Foaming compositions are those compositions which are capable of forming a foam on dispensation from a suitable container, such as a pressurised aerosol container. More preferably are in the form of a hair mousse.

Aerosol-form compositions of the invention will include an aerosol propellant which serves to expel the other materials from the container, and forms the mousse character in mousse compositions. The aerosol propellant included in styling compositions of the present invention can be any liquefiable gas conventionally used for aerosol containers. Examples of suitable propellants include dimethyl ether and hydrocarbon propellants such as propane, n-butane and isobutane. The propellants may be used singly or admixed. Water insoluble propellants, especially hydrocarbons, are preferred because they form emulsion droplets on agitation and create suitable mousse foam densities.

The amount of the propellant used is governed by normal factors well known in the aerosol art. For mousses the level of propellant is generally up to 35%, preferably from 2% to 30%, most preferably from 3% to 15% by weight based on total weight of the composition. If a propellant such as dimethyl ether includes a vapour pressure suppressant (e.g. trichloroethane or dichloromethane), for weight percentage calculations, the amount of suppressant is included as part of the propellant. For aerosol sprays the levels of propellant are usually higher; preferably from 30 to 98 wt % of the total composition, more preferably 50 to 95 wt %.

Preferred propellants are selected from propane, n-butane, isobutane, dimethyl ether and mixtures thereof. Preferably, the propellant comprises dimethyl ether and at least one of propane, n-butane and isobutane.

The method of preparing aerosol hair styling mousse compositions according to the invention follows conventional aerosol filling procedures. The composition ingredients (not including the propellant) are charged into a suitable pressurisable container which is sealed and then charged with the propellant according to conventional techniques.

Compositions of the invention may also take a non-foaming product form, such as a hair styling cream or gel. Such a cream or gel will include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid crosslinked with allylsucrose or allylpentaerythritol as described in U.S. Pat. No. 2,798,053. These polymers are provided by B.F. Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone, hydroxypropyl guar gum, starch and starch derivatives, and other thickeners, viscosity modifiers, gelling agents, etc. It is also possible to use inorganic thickeners such as bentonite or laponite clays.

The hair styling compositions of the invention can contain a variety of non-essential, optional components suitable for rendering the compositions more aesthetically acceptable or to aid use, including discharge from the container, of the product. Such conventional optional ingredients are well known to those skilled in the art, e.g. preservatives such as benzyl alcohol, methyl paraben, propyl paraben and imidazolidinyl urea, fatty alcohols such as cetearyl alcohol, cetyl alcohol and stearyl alcohol, pH adjusting agents such as citric acid, succinic acid, sodium hydroxide and triethanolamine, colouring agents such as any of the FD&C or D&C dyes, perfume oils, chelating agents such as ethylenediamine tetraacetic acid, and polymer plasticising agents such as glycerin and propylene glycol The invention will now be further illustrated by the following, non-limiting Examples.

Examples of the invention are illustrated by a number, comparative examples are illustrated by a letter.

| Chemical name | Trade name | Manufacturer | Act. level % |
|---|---|---|---|
| quaternized vinylpyrrolidone/ dimethylaminoethyl- methacrylate copolymer | Gafquat 734 | ISP | 50% |
| Branched dimethiconol emulsion | DC1787 | DOW CORNING | 55% |
| LPG 0.29 (Propane/Butane) | HARP ® AP40 | HARP INTERNATIONAL | 100% |
| Acrylic co-polymer emulsion | PRIMAL PS83-D | ROHM and HAAS | 53% |
| Ceteareth-50 | Empilan KM50FK | Albright & Wilson | 100% |

| | Example A | Example 1 |
|---|---|---|
| Gafquat 734 | 4% | 2% |
| DC1787 | 3.63% | 3.63% |
| PRIMAL PS83-D | | 1.88% |
| HARP ® AP40 | 8% | 8% |
| surfactant | 0.46% | 0.46% |
| water | water up to 100% | water up to 100% |

A set of six 7 g/10" 'virgin' Spanish hair switches were used. The switches were washed following the protocol: i) 0.7 ml of 16% wt. SLES.2EO solution was applied along the length of the switch hair and agitated for 30 seconds; ii) the switch was then rinsed under warm (30-35° C.) running water for 30 seconds; iii) further 0.7 ml of 16% wt. SLES.2EO solution was applied, followed by 30 seconds of agitation; iv) finally the hair was rinsed for 1 minute. The switches were then towel dried and combed carefully to detangle.

Each switch was treated by application of 0.05 g of mousse per g of hair (0.35 g per switch). The mousse was spread using thumb and forefinger through the length of the switches and rubbed gently to ensure even distribution. Three switches (1-3) were treated with Example 1 and three switches (4-6) were treated with Example A. The switches were then suspended vertically from a clamp stand and dried using a diffuser drier. Each switch was then combed 5 times. One switch from each of the treatments is then presented in a pair to a panel of 9 assessors.

The panellists were asked to assess the amount of flyaway and hair spread out of the switches and make a forced choice (to choose the switch that has less of these attributes). The results were analysed using statistical programme Salon Sys, which uses Chi-square analysis.

Results

| | Preference |
|---|---|
| Example A vs Example 1 | 31:69 (significant) | it is thus demonstrated that the Example according to the invention is preferred.

Comparison to Silicone Pressure Sensitive Adhesives

Materials

| Chemical name | Trade name | Manufacturer | Act. level % |
|---|---|---|---|
| Tricaprylin | PANACET 800 | NOF COPORATION | 100 |
| Pentaerythritol Tetra-2-ethylhexanoate | CETIOL PEEH-4 | COGNIS JAPAN | 100 |
| Polyoxyethylene (10) lauryl ether | EMALEX 710 | NIHON EMULSION | 100 |
| LPG 0.29 (Propane/Butane) | HARP ® AP40 | HARP INTERNATIONAL | 100 |
| Acrylic co-polymer emulsion | PRIMAL PS83-D | ROHM and HAAS | 53 |
| Bio-PSA emulsion | DC ® 5-7200 | DOW CORNING | 60 |
| Bio-PSA emulsion | DC ® 5-7300 | DOW CORNING | 60 |

The silicone PSA emulsions are defined below

| Product code | DC ® 5-7300 18393-45 | DC ® 5-7200 17724-65-A |
|---|---|---|
| % internal phase (solvent + PSA) | 60 | 60 |
| PSA:solvent ratio | 40:60 | 60:40 |
| Solvent | isododecane | 1 cSt PDMS |
| Resin:Polymer ratio | 65:35 | 65:35 |
| Particle size D50 (Microtrack) | 4.312 μm | 10 μm |
| Emulsifier | anionic | anionic |

COMPARATIVE EXAMPLES

| | B | C | D | E | F | G |
|---|---|---|---|---|---|---|
| DC ® 5-7200 | 1.67 | | 1.67 | | 1.67 | |
| DC ® 5-7300 | | 2.5 | | 2.5 | | 2.5 |
| PANACET 800 | | | 0.5 | 0.5 | | |
| CETIOL PEEH-4 | | | | | 0.5 | 0.5 |
| EMALEX | 0.5 | 0.5 | 0.5 | 0.5 | 0.5 | 0.5 |
| CAP40 | 8 | 8 | 8 | 8 | 8 | 8 |
| water | Up to 100 | Up to 100 | Up to 100 | Up to 100 | Up to 100 | Up to 100 |

EXAMPLES

| | 2 | 3 | 4 |
|---|---|---|---|
| PRIMAL PS83-D | 1.13 | 1.13 | 1.13 |
| PANACET 800 | | 0.5 | |
| CETIOL PEEH-4 | | | 0.5 |
| EMALEX | 0.5 | 0.5 | 0.5 |
| CAP40 | 8 | 8 | 8 |
| water | Up to 100 | Up to 100 | Up to 100 |

2 g/10" 'virgin' Spanish hair switches were used. The switches were washed in sets of 5 following the protocol: i) 1 ml of 16% wt. SLES.2EO solution was applied along the length of the wet hair and agitated for 30 seconds; ii) the switches were then rinsed under warm (30-35° C.) running water for 30 seconds; iii) further 1 ml of 16% wt. SLES.2EO solution was applied, followed by 30 seconds of agitation; iv) finally the hair was rinsed for 1 minute. The switches were then towel dried and combed carefully to detangle. The switches were treated in sets of 5 applying 0.1 g of mousse per g of hair (1 g per set). The mousse was spread using thumb and forefinger through the length of the switches and rubbed gently to ensure even distribution. The switches were combed through separately whilst suspended vertically from a clamp stand, each switch was aligned straight and smoothed into tight rod-like bundle by running thumb and forefinger along the length of the switch and then allowed to dry naturally overnight at 20° C. and 50% RH. The switches were then hung against a light panel and photographed. The generated colour digital images were rendered into grey-scale format. The grey-scale images were subsequently converted into a binary form (i.e. composed only of black and white pixels). The dimensionless 2D projection area of each switch was used as a measure of the extent of switch spread out (loss of style). The projection area was calculated from the number of black pixels. 5 switches were used per treatment in each experiment and the results were averaged across the set. Each treatment was tested in three independent experiments and the results were averaged once again.

The data were normalised by taking the ratio of the projection area to the average switch projection area calculated for the set of switches treated with Example 2. One can see from the presented data bellow that the addition that the acrylic pressure sensitive adhesive performs better in the presence of PANACET 800 and CETIOL PEEH in comparison to the silicone pressure sensitive adhesives.

| | | | | Examples | | | | | |
|---|---|---|---|---|---|---|---|---|---|
| 2 | B | C | 3 | D | E | 4 | F | G |
| 1 | 1.7 +/- 0.1 | 1.3 +/- 0.3 | 1.0 +/- 0.5 | 3.3 +/- 0.1 | 3.0 +/- 0.1 | 1.4 +/- 0.4 | 3.2 +/- 0.1 | 3.4 +/- 0.1 |

The following are Examples according to the invention:

Example 5

Aerosol Mousse

| | | |
|---|---|---|
| Gafquat 734 | ICP | 2% |
| DC1787 | Dow Corning | 3.6% |
| Dow Corning PA-0560 | Dow Corning | 2.5% |
| CAP 40 | | 8% |
| Empilan KM50FK | Albright & Wilson | 0.46% |
| water | | water up to 100% |

Example 6

Aerosol Mousse

| | | |
|---|---|---|
| Dow Corning MG-0580 | Dow Corning | 2.5% |
| DC17 87 | Dow Corning | 2.5% |
| IPM | Uniqema | 2% |
| CATION VB-M | NOF Corporation | 0.34% |
| KALCOL 8688 | Kao | 0.32% |
| KALCOL 6870 | Kao | 0.32% |
| EMALEX 710 | Nihon | 1% |
| CAP40 | | 8% |
| water | | Up to 100% |

Example 7

Cream

| | | |
|---|---|---|
| Tackwhite NA 55 | Ichemco SRL | 2.0% |
| DC1787 | Dow Corning | 3.5% |
| monopropylene glycol | ICI Chemicals and Polymers LTD | 3% |
| isopropyl palmitate | Berk LTD | 1% |
| IPM | Uniqema | 0.5% |
| SALCARE SC91 | Allied Colloids | 1.75% |
| water | | Up to 100% |

Example 8

Pump Mousse

| | | |
|---|---|---|
| ACRONAL V212 | BASF | |
| CAPB | Albright and Wilson | 0.35% |
| Tween 20 | Uniqema | 0.25% |
| cremophor RH 410 | BASF | 0.3% |
| DC 193 | Dow Corning | 0.15% |
| Luviquat FC 550 | BASF | 3.75% |
| PVP/VA W735 | GAF Chemicals Corporation | 2% |
| mono propylene glycol | ICI Chemicals and Ppolymers LTD | 2% |
| citric acid | | 0.15% |
| sodium benzoate | | 0.5% |
| water | | to 100% |

Example 9

Cream

| | | |
|---|---|---|
| Acronal V215 | Dow Corning | 2.5% |
| KALCOL 8688 | Kao | 1.5% |
| KALCOL 6870 | Kao | 1.5% |
| Polysurf 67 | Hercules | 0.03% |
| GENAMINE CTAC | Clariant | 2.4% |
| IPM | Uniqema | 1.00% |
| Luviquat FC 550 | BASF | 1.5% |
| DC1787 | Dow Corning | 1.5% |
| Water | | Up to 100% |

The invention claimed is:

1. A hair treatment composition comprising: (1) an acrylic pressure sensitive adhesive, the acrylic pressure sensitive adhesive comprising a random copolymer comprising an acrylic group having a side chain of n-butyl acrylate or 2-ethylhexyl acrylate; methyl acrylate; and acrylic acid wherein said acrylic pressure sensitive adhesive is present in an emulsion; and (2) an emollient, wherein said emollient is selected from the group consisting of tricaprylin, pentaerythritol tetraoctanoate and mixtures thereof.

2. A composition according to claim 1 which is a leave on composition.

3. A composition according to claim 1 which is in the form of a mousse.

4. A hair treatment composition according to claim 3 which further comprises hydrocarbon propellant.

5. A method for styling hair which comprises contacting the hair with a composition in accordance with claim 1.

\* \* \* \* \*